(12) United States Patent
Kilgore et al.

(10) Patent No.: US 10,456,575 B2
(45) Date of Patent: *Oct. 29, 2019

(54) ADJUSTABLE NERVE ELECTRODE

(71) Applicant: Case Western Reserve University, Cleveland, OH (US)

(72) Inventors: Kevin Kilgore, Avon Lake, OH (US); Douglas Michael Ackermann, Jr., Palo Alto, CA (US); Niloy Bhadra, Cleveland Heights, OH (US); Narendra Bhadra, Chesterland, OH (US); Joe Payer, Brecksville, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/973,582

(22) Filed: May 8, 2018

(65) Prior Publication Data
US 2018/0250506 A1 Sep. 6, 2018

Related U.S. Application Data

(60) Division of application No. 15/142,114, filed on Apr. 29, 2016, now Pat. No. 10,039,917, which is a
(Continued)

(51) Int. Cl.
*A61N 1/05* (2006.01)
*A61N 1/36* (2006.01)

(52) U.S. Cl.
CPC ......... *A61N 1/0556* (2013.01); *A61N 1/0551* (2013.01); *A61N 1/36071* (2013.01); *A61N 1/36185* (2013.01)

(58) Field of Classification Search
CPC ...... A61N 1/05; A61N 1/0551; A61N 1/0556; A61N 1/36; A61N 1/3607; A61N 1/36071; A61N 1/36185
(Continued)

(56) References Cited

U.S. PATENT DOCUMENTS

| 5,578,061 A | 11/1996 | Stroetmann et al. |
| 7,502,652 B2 | 3/2009 | Gaunt et al. |

(Continued)

FOREIGN PATENT DOCUMENTS

WO 2009/058258 A1 5/2009

*Primary Examiner* — Christopher A Flory
(74) *Attorney, Agent, or Firm* — Tarolli, Sundheim, Covell & Tummino LLP

(57) ABSTRACT

Example adjustable electrodes are described. One example adjustable electrode includes two or more contacts configured to selectively deliver high frequency alternating current (HFAC) to a nerve in an amount sufficient to produce an HFAC nerve conduction block in the nerve. The example adjustable electrode may also include a logic configured to selectively control which of the two or more contacts deliver HFAC to the nerve to control whether the nerve electrode is in a first (e.g., onset response mitigating) configuration or in a second (e.g., HFAC nerve conduction block maintenance) configuration. The electrode may be used in applications including, but not limited to, nerve block applications, and nerve stimulation applications. The electrode may be adjusted by changing attributes including, but not limited to, the number, length, orientation, distance between, surface area, and distance from a nerve of contacts to be used to deliver the HFAC.

10 Claims, 8 Drawing Sheets

Related U.S. Application Data continuation of application No. 14/463,948, filed on Aug. 20, 2014, now Pat. No. 9,364,661, which is a division of application No. 12/948,848, filed on Nov. 18, 2010, now Pat. No. 8,843,188.

(60) Provisional application No. 61/263,592, filed on Nov. 23, 2009.

(58) Field of Classification Search
USPC .................. 600/372; 607/2, 45, 46, 72, 118
See application file for complete search history.

(56) References Cited

U.S. PATENT DOCUMENTS

| | | | |
|---|---|---|---|
| 8,082,039 B2 | 12/2011 | Kim et al. | |
| 8,983,614 B2 | 3/2015 | Kilgore et al. | |
| 9,913,987 B2* | 3/2018 | Lee | A61N 1/06 |
| 2004/0093093 A1 | 5/2004 | Andrews | |
| 2004/0243182 A1 | 12/2004 | Cohen et al. | |
| 2005/0131485 A1 | 6/2005 | Knudson et al. | |
| 2005/0149148 A1 | 7/2005 | King | |
| 2006/0030919 A1 | 2/2006 | Mrva et al. | |
| 2006/0085049 A1 | 4/2006 | Cory et al. | |
| 2007/0043400 A1 | 2/2007 | Donders et al. | |
| 2007/0219546 A1 | 9/2007 | Mody et al. | |
| 2008/0058888 A1 | 3/2008 | King | |
| 2009/0036945 A1 | 2/2009 | Chancellor et al. | |
| 2009/0118789 A1* | 5/2009 | Buhlmann | A61N 1/0452 607/46 |
| 2009/0204173 A1 | 8/2009 | Fang et al. | |
| 2009/0222053 A1 | 9/2009 | Gaunt et al. | |
| 2010/0016929 A1 | 1/2010 | Prochazka | |
| 2010/0036454 A1 | 2/2010 | Bennett et al. | |
| 2010/0114244 A1 | 5/2010 | Manda et al. | |
| 2010/0114254 A1 | 5/2010 | Kornet | |
| 2010/0125313 A1 | 5/2010 | Lee et al. | |
| 2010/0145253 A1 | 6/2010 | Gutsol et al. | |
| 2010/0152808 A1 | 6/2010 | Boggs, II | |
| 2010/0241190 A1* | 9/2010 | Kilgore | A61N 1/205 607/48 |
| 2010/0298920 A1 | 11/2010 | Mrva et al. | |
| 2011/0082383 A1 | 4/2011 | Cory et al. | |
| 2011/0125216 A1 | 5/2011 | Kilgore et al. | |
| 2011/0152956 A1* | 6/2011 | Hincapie Ordonez | A61N 1/3627 607/4 |
| 2012/0016448 A1 | 1/2012 | Lee | |
| 2012/0041509 A1* | 2/2012 | Knudson | A61N 1/05 607/40 |

* cited by examiner

ADJUSTABLE NERVE ELECTRODE

PRIORITY CLAIM

This application is a divisional of U.S. patent application Ser. No. 15/142,114, filed Apr. 29, 2016, which is a continuation of U.S. patent application Ser. No. 14/463,948, filed Aug. 20, 2014 (Now U.S. Pat. No. 9,364,661), which is a divisional of U.S. application Ser. No. 12/948,848 filed on Nov. 18, 2010 (Now U.S. Pat. No. 8,843,188), which claims the benefit under 35 USC § 119(e) to U.S. Provisional Application 61/263,592, filed Nov. 23, 2009, all of which are hereby wholly incorporated by reference.

FEDERAL FUNDING NOTICE

The invention was developed with federal funding supplied under Federal Grant No. R01-EB002091 provided by the National Institute of Biomedical Imaging and Bioengineering of the National Institute of Health. The Federal Government has certain rights in the invention.

BACKGROUND

Undesired or pathological hyperactivity in the peripheral nervous system occurs in many disorders and diseases. This undesired or pathologic hyperactivity may result in undesired motor or sensory effects. Additionally, some medical conditions resulting in chronic pain (e.g., neuromas) are characterized by undesired afferent activity in peripheral nerves. Treatment may include blocking the conduction of these pathological or undesirable signals to mitigate the effects of these conditions. However, conventional conduction blocks may have employed conventional fixed electrodes that are not adjustable and that lead to undesired side effects.

Conventional nerve electrodes have produced undesired side effects in nerve blocking and nerve stimulating applications. The undesired side effects may include, for example, tissue damage. The damage may occur, for example, due to the size and orientation of electrode contacts. The damage may also occur, for example, due to the fact that conventional electrodes carry current via electrons while nerve tissues carry current via ions. (See, for example, Krames, Elliot S., Neuromodulation, Academic Press, 072009. 152.)

Uncoordinated or unwanted generation of nerve impulses is a major disabling factor in many medical conditions. For example, uncoordinated motor signals produce spasticity in stroke, cerebral palsy and multiple sclerosis, resulting in the inability to make functional movements. Involuntary motor signals in conditions such as tics and choreas produce incapacitating movements. Undesirable sensory signals can result in peripherally generated pain. Over-activity in the autonomic nervous system can produce conditions such as hyperhydrosis. If these nerve impulses can be interrupted along the peripheral nerves in which they travel, these disabling conditions can be managed or eliminated.

Conventional nerve blocks that prevent the propagation of an action potential through a nerve have been achieved using high frequency alternating current (HFAC), using single phase current (e.g., direct current), and through combinations thereof. HFAC, where the frequency ranges between, for example, 2 kHZ and 50 kHZ, can completely yet reversibly block the motor fibers in a peripheral nerve. In a conventional nerve blocking apparatus, HFAC is typically delivered through one or more conventional electrodes, which has provided sub-optimal results due, at least in part, to the design of the conventional fixed electrodes. Conventional fixed (e.g., non-adjustable) electrodes may have been designed with tradeoffs concerning the conflicting goals of mitigating onset response and maintaining an HFAC block.

A block threshold is defined as the lowest amplitude at which an entire nerve is blocked. The block threshold increases directly with frequency. If the HFAC amplitude is above the block threshold, then the conduction block will be maintained. There is an amplitude region below the block threshold where the HFAC produces a significant and prolonged nerve activity. This activity occurs where the HFAC is approximately 50-70% of the block threshold. Minimizing the block threshold facilitates having an HFAC block with a minimal charge injection to the nerve and with minimal power requirements.

HFAC produces a focal block at the site of the electrode, The block is quickly reversible, usually within one second, and is fast acting, usually appearing in less than a couple of seconds. An HFAC nerve block induces an intense neural volley at the onset of HFAC delivery before block occurs. This is referred to as the onset response. The blocking waveform typically used in mammalian experiments is a 2 kHz-40 kHz sinusoidal or square wave with an amplitude of 3 V-10 V, or 1 mA-10 mA for current-controlled studies, with higher frequencies requiring higher amplitudes to achieve block.

Substantially reducing or eliminating the onset response will facilitate making HFAC block more viable for clinical applications. It is desirable to prevent the onset activity from occurring for both motor and sensory applications, because it is likely to result in extreme pain and activation of an innervated end effector (e.g., a muscle).

The onset response is characterized by two phases that are usually distinct. The first phase, "Phase I," is always present if neural conduction block is achieved. Phase I is characterized by a brief (e.g., tens of msec) and intense neural volley. This intense neural volley manifests itself as a large muscle twitch in whole nerve/muscle preparations. The second phase of the onset response, "Phase II," is characterized by repetitive firing in the nerve that occurs after the intense volley of Phase I and can last for tens of seconds. In most cases, the nerve accommodates to the HFAC and the repetitive firing diminishes gradually into quiescence. This activity has been demonstrated in both whole nerve/muscle and single fiber preparations.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
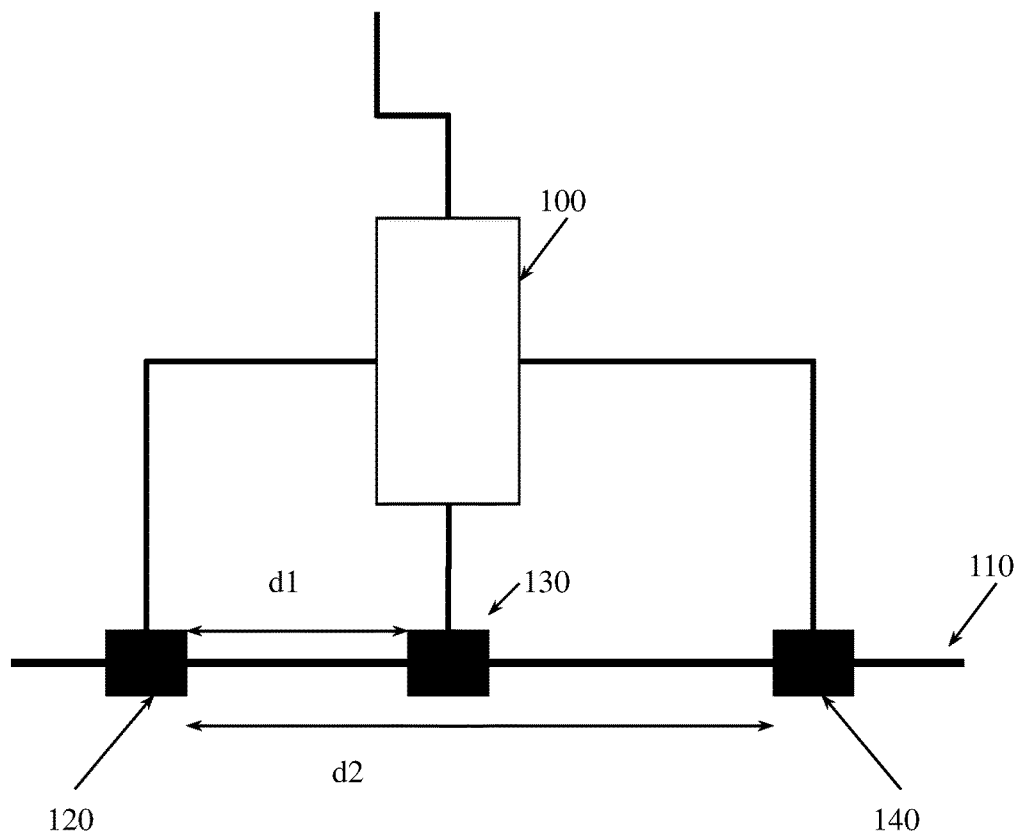
FIG. 1 illustrates an example adjustable nerve electrode.

This application describes electrodes with adjustable geometries. Geometric parameters of the electrode or electrodes used to produce the HFAC nerve block affect the duration of the initial period. The geometric parameters include the surface area of a contact, the shape of a contact, the distance between contacts, the distance between a contact and a nerve, and so on. Geometric parameters of the electrode or electrodes used to produce the HFAC nerve block also affect the ability to maintain the HFAC nerve block. Conventionally, designing an electrode to have geometric parameters that positively affect the duration and/or intensity of the onset response has negatively impacted the ability to maintain an HFAC nerve block, and vice versa. Therefore, example electrodes may be adjustable in different geometric parameters including, but not limited to, surface area of contacts, shape of contacts, distance between contacts, and distance between contacts and nerve tissue. Being able to adjust the electrode facilitates placing it in a first configuration that addresses onset response issues and then placing it in a second configuration that addresses maintaining HFAC nerve block issues.

Example electrodes are configurable. An example electrode can be placed in a first configuration to positively impact the onset response and then can be reconfigured to a second configuration that will positively impact the ability to maintain the HFAC. In one example, geometric properties of an electrode can be adjusted through remote electrical switches. For example a switch can be manipulated that changes the distance between contacts. In another example, geometric properties of an electrode are automatically adjusted by a control program associated with the electrode. For example, a program can automatically adjust the distance between contacts after a pre-programmed period of time.

"Adjusting the distance between contacts" can be achieved electrically rather than mechanically. Consider the electrode illustrated in FIG. 1. One portion 100 of the electrode receives an input signal and selectively provides an output signal to nerve 110 through one or more of contact 120, contact 130, and contact 140. The contacts through which the output signal is provided to nerve 110 can be changed over time. For example, at a first point in time, the output signal may be provided through contacts 120 and 130 and at a second point in time the output signal may be provided through contacts 120 and 140. When the output signal is provided through contacts 120 and 130 the output signal is provided through contacts that are more closely spaced than when the output signal is provided through contacts 120 and 140. The distance between the contacts can affect the initial activity and/or the ability to maintain an HFAC block.

While FIG. 1 illustrates three contacts, one skilled in the art will appreciate that an electrode can have a greater number of contacts. Additionally, while FIG. 1 illustrates all three contacts being substantially the same size and shape, one skilled in the art will appreciate that an electrode can have contacts that have different sizes, different shapes, different materials, and that are spaced and oriented differently.

Figure 2:
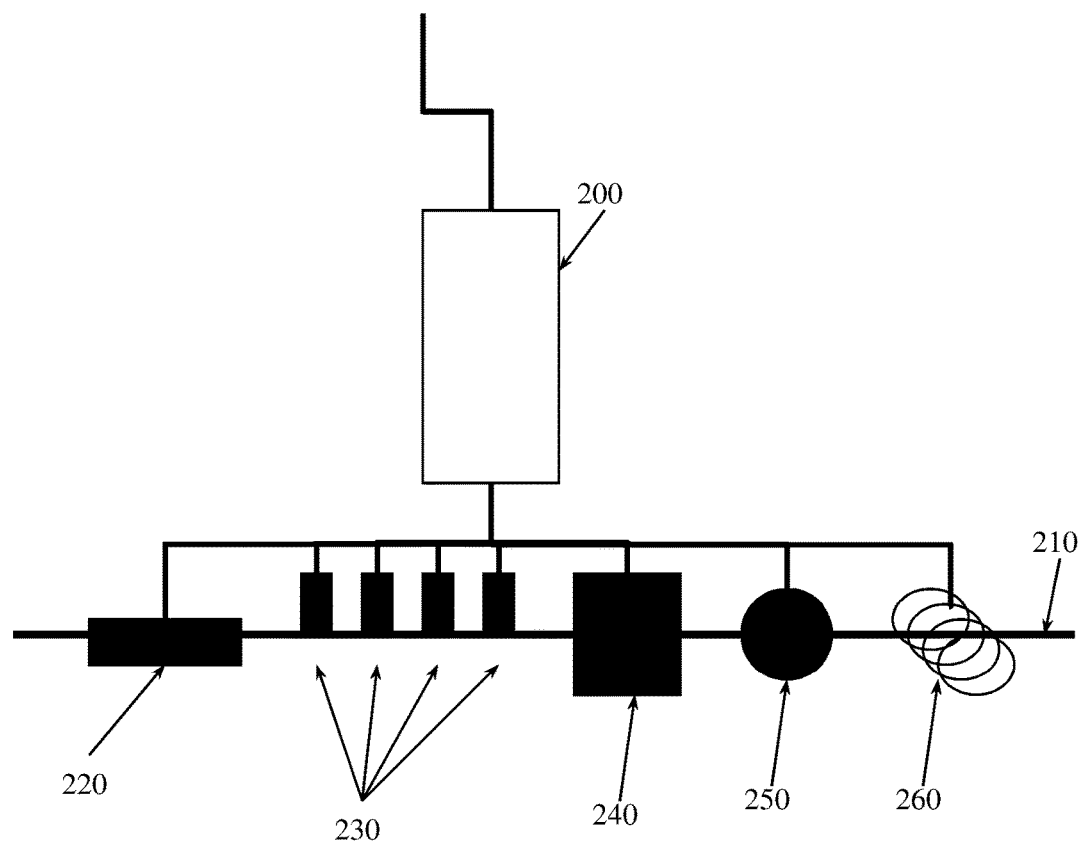
FIG. 2 illustrates an example adjustable nerve electrode.

FIG. 2 illustrates an electrode with multiple contacts having different properties. A portion 200 receives an input signal and selectively provides an output signal to nerve 210 through contacts 220, contact set 230, contact 240, contact 250, and/or contact 260. At different times the signal can be provided through different combinations of contacts. For example, at a first time the output signal could be provided through contact set 230, which may be designed to minimize onset activity, while at a second time the output signal could be provided by rotating through contacts 220, 240, 250, and 260. Thus, one skilled in the art will appreciate that different combinations of contacts can be used at different times for different purposes.

A contact can be, for example, cylindrical and encircle a nerve (see, e.g., contact 250). A contact can also be, for example, a spiral that winds around a nerve (see, e.g., contact 260). One skilled in the art will appreciate that variable configurations can be produced from different contacts having different sizes, shapes, geometries, materials, and signal delivering properties.

An adjustable electrode may be adjusted, for example, to increase or decrease the surface area through which a signal is applied. To increase surface area a greater number of contacts may be used or a larger contact may be used. To decrease surface area a lesser number of contacts may be used or a smaller contact may be used. For example, if the output signal is being applied only through contacts 230, then a first configuration designed to minimize onset response may use a minimal surface area by using only two of the four contacts. However, a second configuration designed to maximize the ability to maintain an HFAC may use all four of the contacts. In another embodiment, rather than using all four of the contacts, the adjustable electrode may rotate through three of the four contacts in a pattern that facilitates maintaining an HFAC block while reducing damage associated with prolonged metal to tissue contact.

Figure 3:
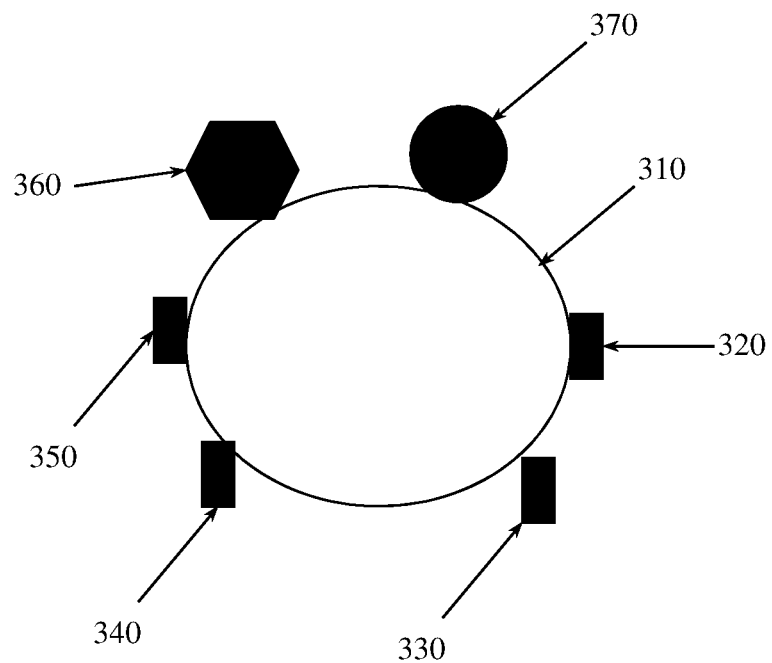
FIG. 3 illustrates an example adjustable nerve electrode.

FIG. 3 illustrates a different view of a nerve 310. This view illustrates that different types of contacts can be arranged in different ways and in different locations around nerve 310. For example, an output signal can be applied to nerve 310 using one or more of contacts 320, 330, 340, 350, 360, and 370. Thus, an adjustable electrode may switch between contacts based on their location along a nerve and/or based on their location around a nerve. The ability to selectively apply an output signal to different contacts may facilitate selectively applying the signal to certain portions of a nerve rather than to an entire nerve.

One skilled in the art will appreciate that different contacts can be different types of contacts. For example, contact 320 could be a traditional platinum metal to tissue contact while contact 330 could be a contact that employs an ionically conductive material.

Figure 4:
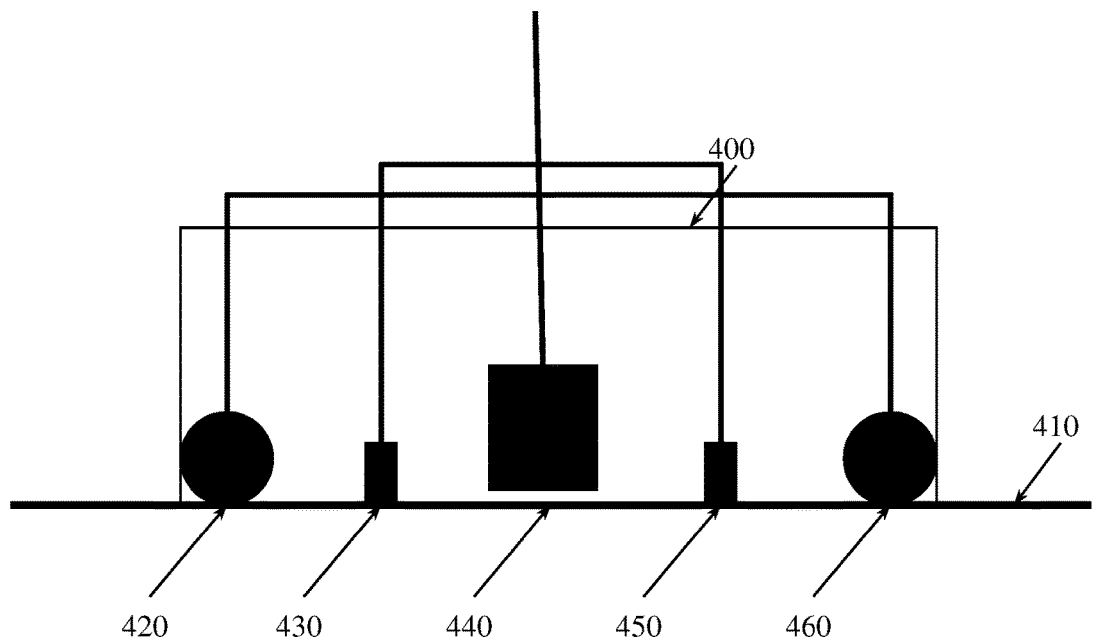
FIG. 4 illustrates an example adjustable nerve electrode.

One skilled in the art will also appreciate that different apparatus could combine an adjustable electrode with selectively controllable cooling devices. FIG. 4 illustrates an example apparatus 400 interfacing with a nerve 410. Apparatus 400 includes two selectively controllable cooling devices 420 and 460. Apparatus 400 also includes three contacts 430, 440, and 450. Cooling devices 420 and 460 can have different cooling capacities, can operate according to different principles, and may be appropriate for different types of cooling to produce different types of blocks. Similarly, contacts 430, 440, and 450 can be different types of contacts made of different materials and having different sizes, shapes, and geometries. Therefore, apparatus 400 can be a configurable electrode that can select which, if any, cooling devices to employ and which, if any, contacts to apply to perform nerve blocking including, but not limited to, cooling based nerve blocking, HFAC nerve blocking, cooling+HFAC nerve blocking, DC nerve blocking, DC+HFAC nerve blocking, and cooling+DC+HFAC nerve blocking. Apparatus 400 can, over the course of a nerve block, use different combinations of the cooling devices and/or contacts in the apparatus 400 to alter onset affects, to prolong blocking, to alter blocking, and to manipulate other controllable factors.

There is a relationship between monopolar electrode contact length and block threshold in an HFAC nerve conduction block. The contact length of a monopolar electrode has an effect on the threshold current required to achieve conduction block. The contact separation distance of a bipolar nerve cuff electrode influences the threshold current required to achieve a nerve block. Block thresholds are minimized when electrode geometry maximizes neuronal membrane depolarization.

The minimal current required to block a nerve or nerve fiber is referred to as the "block threshold". Minimizing the block threshold may result in less power consumption by an implanted device. Minimizing the block threshold may also have implications for achieving a safe blocking paradigm since lower currents are generally associated with a safer stimulation protocol. The block threshold is affected by the frequency of the waveform, the diameter of the fiber being blocked, the electrode-fiber distance, and the longitudinal orientation of an electrode relative to a node of Ranvier. Block threshold is also affected by the geometry of the blocking electrode, specifically the interpolar spacing of a multipolar nerve cuff electrode. Block threshold can be reduced by using an electrode geometry that maximizes membrane depolarization. This can be achieved by maximizing two factors: the extracellular activating function produced by the electrode, and the degree of synergistic contribution to membrane depolarization by sodium currents at multiple nodes of Ranvier. The longitudinal contact length of a monopolar electrode also affects the block threshold.

Experimental results have demonstrated that nerve conduction block using HFAC can be reliably and repetitively achieved with a monopolar nerve cuff electrode. Nerve block is possible using intrafascicular microwires. An intrafascicular electrode, or a traditional cylindrical "percutaneous" style peripheral nerve electrode can be employed in a monopolar configuration. The length of a monopolar electrode contact was shown to affect the threshold current required to achieve conduction block in both the whole nerve preparation and in simulation. The experimentally measured block thresholds show that the minimal mean block threshold occurred for a monopolar contact length of approximately 1.0 mm.

Nerve cuff electrode geometry has an effect on onset response. Both the separation distance between two bipolar electrode contacts and the contact length of a monopolar electrode contact have a significant effect on onset response magnitude and duration. The length of an electrode contact, like the separation distance for a bipolar electrode, can be optimized to depolarize the fibers in a nerve to a blocked state with minimal current. Block thresholds continually increase with monopolar contact length, whereas they asymptotically plateau with large bipolar separations. This monopolar trend occurs because larger currents must be used to compensate for a large electrode area for a long monopolar electrode contact. Block thresholds are minimized by maximizing intracellular depolarization for a given electrode current.

Electrode design considers minimizing the onset response and minimizing the total charge needed to produce a nerve block. For bipolar electrodes, block threshold was shown both experimentally and in single fiber simulation to exhibit a U-shaped trend with bipolar separation distance with the minimum thresholds occurring for separation distances of 1.0-2.0 mm. Some electrode configurations (e.g. a bipolar separation of 0.5 mm) are better for producing a block with a small onset response and others (e.g. a bipolar separation of 2.0 mm) are better for producing a block with a low block threshold. The weighting of magnitude of onset response versus total charge injection may depend on the clinical application. For example, criteria for developing a therapy that is intended for individuals without sensation (e.g. a bladder voiding prosthesis for the paralyzed) would likely favor a minimization of power consumption over minimizing the magnitude of the onset response.

When current is delivered through a nerve cuff electrode, a large field intensity is produced at the site of the electrode contacts, and a lesser, but significant, "virtual electrode" field intensity occurs at the edges of the cuff. The geometry of a nerve cuff electrode and the amplitude of HFAC affect the intensity of these virtual electrode fields. Neurons subjected to HFAC with an amplitude that is subthreshold for block undergo rapid firing. The firing rate decreases with an increase in subthreshold HFAC amplitude (above 50% of block threshold). The intensity of these subthreshold fields would increase with an increase in blocking current amplitude.

The temporal decay in Phase II firing may occur due to a slow membrane depolarization for axons subjected to subthreshold field intensities. This slow depolarization may be caused by an accumulation of potassium in the extracellular space. Extracellular potassium accumulation is known to cause membrane depolarization, and has been associated with conduction block in central nervous system neurons. Extracellular potassium accumulates in peripheral nerves when they undergo high rates of firing. This accumulation may result in the decay in firing rate seen in Phase II of the onset response.

The contact separation distance of a bipolar nerve cuff electrode, and the contact length of a monopolar electrode have a significant effect on the onset firing response to a HFAC blocking waveform. Interpolar separation distance for a bipolar electrode influences the current amplitudes required to achieve conduction blocks. The minimal current required to achieve block depends on the diameter of the fibers being blocked and the electrode-fiber distance. Minimizing the block threshold may be achieved by maximizing both the bipolar activating function by adjusting the bipolar electrode contact separation distance and the addition of membrane sodium currents generated by the two bipolar electrode contacts.

Block thresholds have a non-linear relationship with bipolar electrode contact separation distance. There is a narrow range of bipolar separations for which the block threshold has a minima. The minimal current required to achieve block depends on the diameter of the fibers being blocked. The minimal current required to achieve block depends on electrode-fiber distance. Minimizing the block threshold may be achieved by maximizing both the bipolar activating function and an augmentative interaction between inward sodium currents generated by each of the two bipolar electrode contacts.

Figure 5:
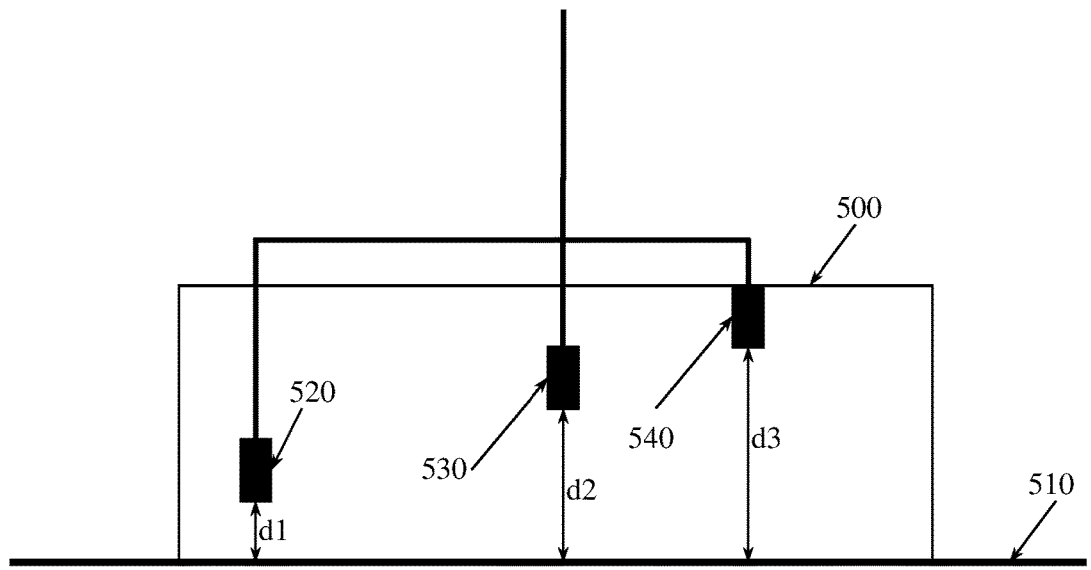
FIG. 5 illustrates an example adjustable nerve electrode.

FIG. 5 illustrates an example adjustable electrode 500 that is used to apply HFAC to a nerve 510. The electrode 500 has three contacts, contact 520, contact 530, and contact 540, through which HFAC can selectively be applied to the nerve 510. Contact 520 is located a first distance d1 from the nerve 510, while contact 530 is a greater distance d2 from the nerve 510 and contact 540 is an even greater distance d3 from the nerve 510. Since the block threshold and maintenance threshold can vary based on the distance from a contact(s) that is applying HFAC to a nerve and the nerve, electrode 500 is configurable to use different of the contacts at different times and for different purposes. For example, for a nerve of a first diameter, contact 520 may be used to establish an HFAC nerve block and contact 540 may be used to maintain the HFAC nerve block. For a nerve of a second diameter, contact 530 may be used to establish an HFAC nerve block and contact 540 may be used to maintain the HFAC block. While three contacts having three different distances are described, one skilled in the art will appreciate that a greater and/or lesser number of contacts positioned at distances greater and/or lesser than those illustrated may be employed. Additionally, one skilled in the art will appreciate that contacts may be positioned to have different orientations to a nerve (e.g., parallel, perpendicular).

Figure 6:
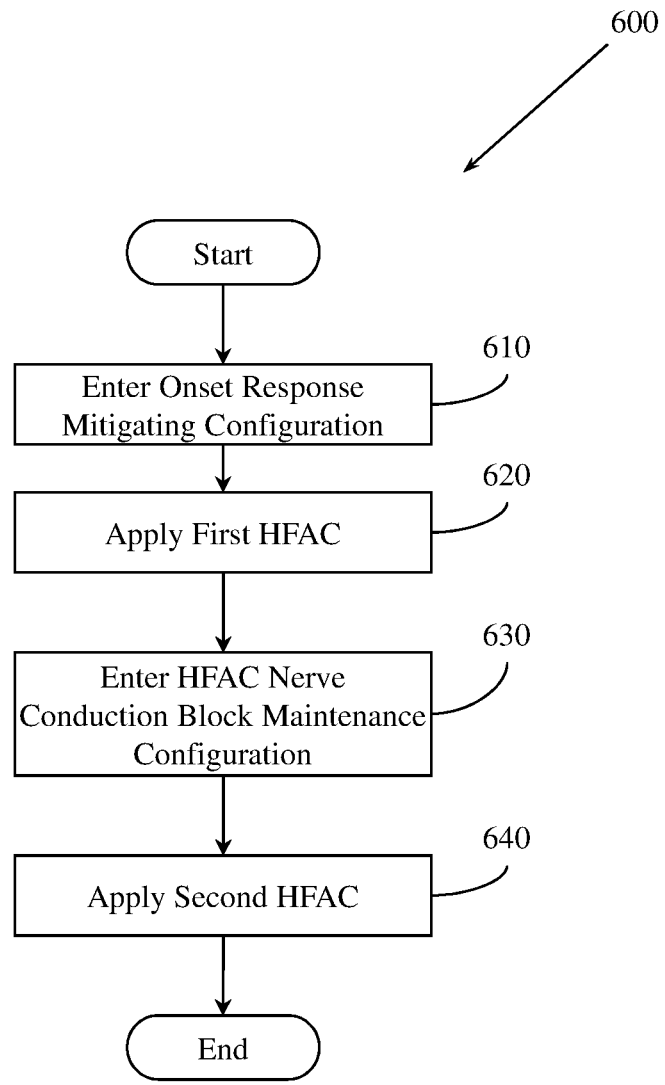
FIG. 6 illustrates an example method associated with an HFAC nerve conduction block produced and maintained by an adjustable nerve electrode.

FIG. 6 illustrates a method 600. Method 600 includes, at 610 controlling an adjustable nerve electrode to enter an onset response mitigating configuration. In one example, controlling the adjustable nerve electrode to enter the onset response mitigating configuration at 610 includes controlling the geometry of a set of contacts in the adjustable nerve electrode. The set of contacts are configurable to selectively apply HFAC to the nerve. Thus, different contacts can be employed to apply HFAC at different times. Controlling the geometry of the set of contacts may include, for example, selecting a first subset of the set of contacts to deliver the first HFAC. The subset may be chosen to facilitate, for example, mitigating the intensity and/or duration of the onset response. The subset may also be chosen, for example, to minimize the threshold current, to maximize neuronal membrane depolarization in the nerve, to maximize extracellular activation function performed by the electrode, to maximize the degree of synergistic contribution to membrane depolarization by sodium currents at multiple nodes of Ranvier in the nerve, and for other reasons. The subset may also be chosen, for example, to minimize power consumption.

Recall from figures one through five that different contact configurations and positions are possible. By choosing different subsets of contacts, different geometries are possible. For example, different surface areas, different orientations, different distances between contacts, different distances between a contact and a nerve, and other attributes may be manipulated. Therefore, in different examples, the first subset may be selected as a function of attributes including, but not limited to, a desired number of contacts to be used to deliver the first HFAC, a desired length of a contact to be used to deliver the first HFAC, a desired distance between contacts to be used to deliver the first HFAC, a desired surface area of a contact to be used to deliver the first HFAC, a desired shape of a contact to be used to deliver the first HFAC, and a desired distance between a contact and the nerve.

In one example, the adjustable nerve electrode is controlled to enter the onset response mitigating configuration at 610 in response to a control signal provided from entities including, but not limited to, a circuit external to the electrode, a circuit internal to the electrode, a control logic external to the electrode, and a control logic internal to the electrode. Thus, the electrode may be externally controlled by, for example, a user manipulated switch, an external circuit, an external computer controller, and so on. Additionally, and/or alternatively, the electrode may be internally controlled by a control circuit, a control logic, and so on.

Method 600 also includes, at 620, applying a first high frequency alternating current (HFAC) through the adjustable nerve electrode while the adjustable nerve electrode is in the onset response mitigating configuration. The first HFAC will have a threshold current sufficient to establish an HFAC nerve conduction block in a nerve. One skilled in the art will appreciate that the HFAC may be associated with different waveform types (e.g., sinusoidal, rectangular, triangular) having different frequencies, amplitudes, and continuities.

Method 600 also includes, at 630, controlling the adjustable nerve electrode to enter an HFAC nerve conduction block maintenance configuration. In one example, controlling the adjustable nerve electrode to enter the HFAC nerve conduction block maintenance configuration at 630 comprises controlling the geometry of the set of contacts in the adjustable nerve electrode. Once again, controlling the geometry of the set of contacts can include selecting a second subset of the set of contacts to deliver the second HFAC. Like the first subset may be selected to achieve certain goals (e.g., minimize onset response), the second subset may also be selected to achieve certain goals. For example, the second subset may be chosen to minimize the HFAC required to maintain the HFAC nerve conduction block, to minimize power consumption, and so on. Different geometries may be appropriate for different types of nerves, different sizes of nerves, and so on. Therefore, in different examples, the second subset may be selected as a function of attributes including, but not limited to, a desired number of contacts to be used to deliver the second HFAC, a desired length of a contact to be used to deliver the second HFAC, a desired orientation of a contact, a desired distance between contacts to be used to deliver the second HFAC, a desired surface area of a contact to be used to deliver the second HFAC, a desired shape of a contact to be used to deliver the second HFAC, and a desired distance between a contact and the nerve.

Method 600 also includes, at 640, applying a second HFAC through the adjustable nerve electrode while the adjustable nerve electrode is in the HFAC nerve conduction block maintenance configuration. The second HFAC will have a current sufficient to maintain the HFAC nerve conduction block in the nerve.

Figure 7:
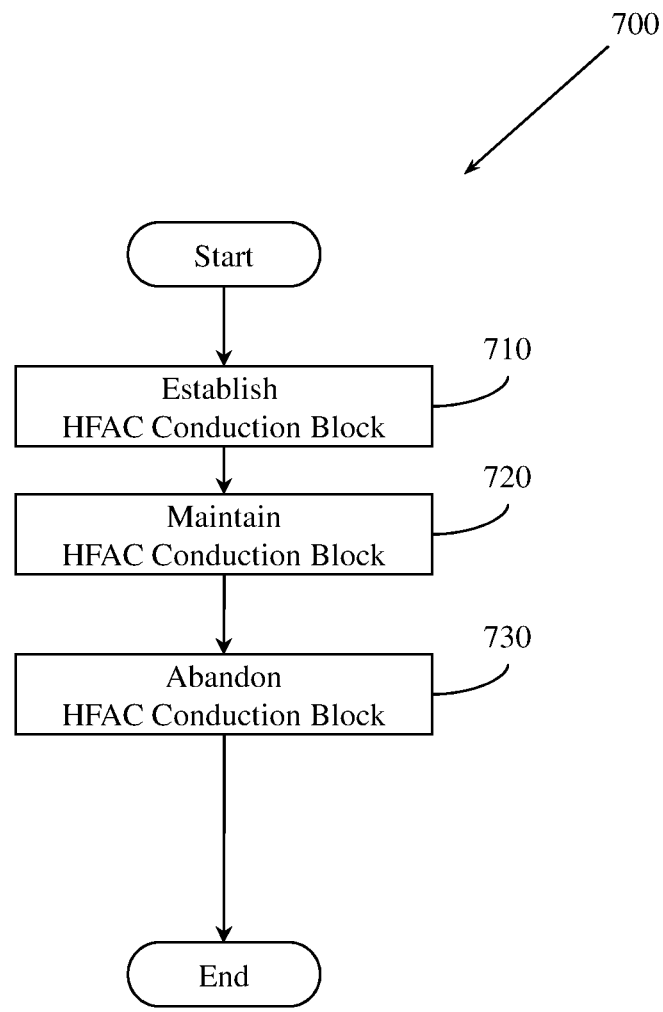
FIG. 7 illustrates an example method associated with an HFAC nerve conduction block produced and maintained by an adjustable nerve electrode.

FIG. 7 illustrates a method 700. Method 700 includes suppressing conduction in a nerve by applying an HFAC block through a variable geometry nerve electrode having a set of contacts that are configurable to selectively apply HFAC to a nerve. Thus, selected members of the set of contacts may be controlled to selectively apply HFAC. The HFAC block and the variable geometry nerve electrode are configured to facilitate recovery of conduction in the nerve substantially instantaneously after removal of the HFAC block.

Thus, method 700 includes, at 710, establishing the HFAC block by applying a first HFAC to the nerve. The first HFAC has a threshold current sufficient to establish the HFAC block. The threshold current will be impacted by the geometry of the electrode. For example, the number, type, size, shape, and positions of the contacts that are used to apply the HFAC will affect the threshold current. Thus, the first HFAC is applied while the variable geometry nerve electrode is in a first geometry that is defined by attributes including, but not limited to, a first number of contacts used to apply the first HFAC, a first distance between contacts used to apply the first HFAC, a first surface area of contacts used to apply the first HFAC, a first shape of a contact used to apply the first HFAC, a first length of a contact used to apply the first HFAC, a first orientation of a contact, and a first distance between a contact and the nerve.

Method 700 also includes, at 720, maintaining the HFAC block by applying a second HFAC to the nerve. The second HFAC will have a current sufficient to maintain the HFAC block. The current sufficient to maintain the HFAC block will be determined by the geometry of the electrode. Thus, the second HFAC is applied while the variable geometry nerve electrode is in a second geometry that is defined by attributes including, but not limited to, a second number of contacts used to apply the second HFAC, a second distance between contacts used to apply the second HFAC, a second surface area of contacts used to apply the second HFAC, a second shape of a contact used to apply the second HFAC, a second length of a contact used to apply the second HFAC, a second orientation of a contact, and a second distance between a contact and the nerve.

The first and second geometries can be selected to achieve different goals. For example, the first geometry may be selected to minimize the threshold current by maximizing neuronal membrane depolarization in the nerve and the second geometry may be selected to minimize the second HFAC.

Figure 8:
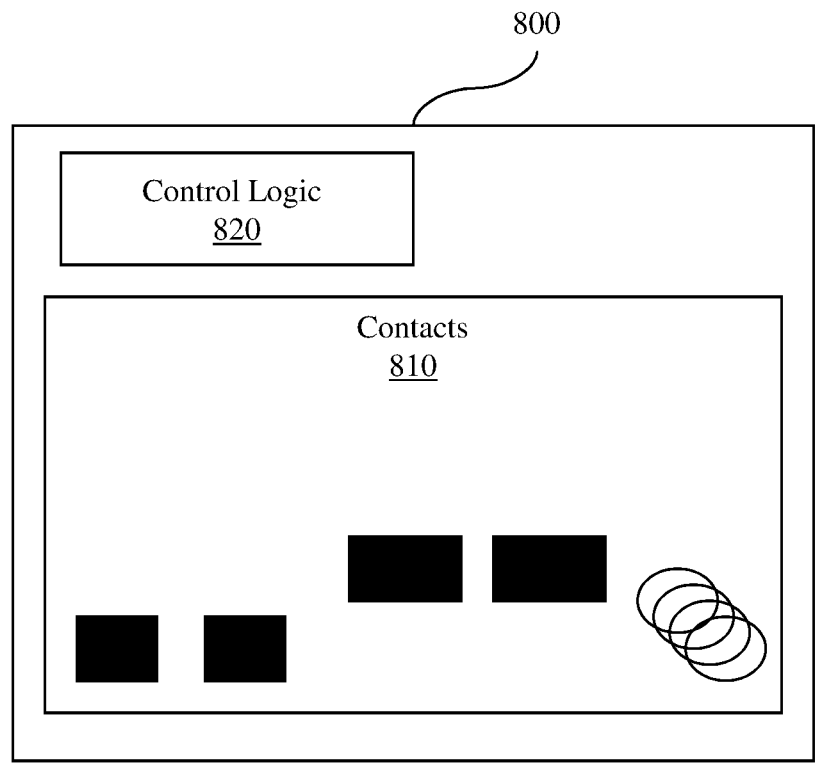
FIG. 8 illustrates an example adjustable nerve electrode.

FIG. 8 illustrates an electrode 800. Electrode 800 includes two or more contacts 810. The two or more contacts 810 are configured to selectively deliver high frequency alternating current (HFAC) to a nerve in an amount sufficient to produce an HFAC nerve conduction block in the nerve. Members of the two or more contacts 810 can have different sizes, shapes, lengths, orientations, distances from each other, distances from a nerve, surface areas, and other attributes.

Electrode 800 also includes a logic 820 that is configured to selectively control which of the two or more contacts 810 deliver HFAC to the nerve. Controlling which members of the two or more contacts 810 deliver the HFAC controls whether the nerve electrode is in an onset response mitigating configuration or an HFAC nerve conduction block maintenance configuration.

In one example, the onset response mitigating configuration is configured to minimize a threshold current required to establish the HFAC nerve conduction block. In another example, the onset response mitigating configuration is configured to maximize neuronal membrane depolarization in the nerve. In yet another example, the onset response mitigating configuration is actually designed to minimize power consumption. The onset response mitigating configuration may be defined by, for example, a desired number of contacts to be used to deliver the HFAC, a desired length of a contact to be used to deliver the HFAC, a desired distance between contacts to be used to deliver the HFAC, a desired surface area of a contact to be used to deliver the HFAC, a desired shape of a contact to be used to deliver the HFAC, and a desired distance between a contact and the nerve.

In one example, the HFAC nerve conduction block maintenance configuration is configured to minimize a current required to maintain the HFAC nerve conduction block. The HFAC nerve conduction block maintenance configuration may also be configured to minimize power consumption. The HFAC nerve conduction block maintenance configuration may be defined by a desired number of contacts to be used to deliver the HFAC, a desired length of a contact to be used to deliver the HFAC, a desired distance between contacts to be used to deliver the HFAC, a desired surface area of a contact to be used to deliver the HFAC, a desired shape of a contact to be used to deliver the HFAC, and a desired distance between a contact and the nerve.

In different examples, control logic 820 may itself be controlled either internally and/or externally. For example, control logic 820 may be controlled to select contacts to apply HFAC to the nerve in response to an external signal originating external to the electrode and/or in response to an internal signal originating internal to the electrode.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, A&B, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A method comprising:
    adjusting a geometric configuration of an adjustable electrode to arrange two or more contacts around a nerve in an onset response mitigating configuration;
    applying an electrical waveform to the nerve;
    blocking an onset response of the electrical waveform due to the onset response mitigating configuration;
    after a period of time, adjusting the geometric configuration of the adjustable electrode to arrange the two or more contacts around the nerve in a block maintenance configuration and
    maintaining a nerve conduction block to the nerve.

2. The method of claim 1, wherein the electrical waveform comprises a high frequency alternating current (HFAC) waveform.

3. The method of claim 1, wherein the onset response mitigating configuration is arranged to maximize neuronal membrane depolarization in the nerve.

4. The method of claim 1, wherein the block maintenance configuration is arranged to minimize a current required to maintain the nerve conduction block.

5. The method of claim 1, wherein the electrical waveform comprises a first high frequency alternating current (HFAC) waveform applied with the onset mitigating configuration and a second HFAC waveform applied with the block maintenance configuration.

6. The method of claim 5, wherein the second HFAC waveform comprises a current sufficient to maintain the nerve conduction block.

7. The method of claim 5, wherein the first HFAC waveform comprises a threshold sufficient to establish the nerve conduction block.

8. The method of claim 1, wherein the adjustable electrode changes configurations based on control logic.

9. The method of claim 8, wherein the control logic is signaled from a source internal to the adjustable electrode.

10. The method of claim 8, wherein the control logic is signaled from a source external to the adjustable electrode.

* * * * *